United States Patent [19]

Milo

[11] Patent Number: 5,403,338
[45] Date of Patent: Apr. 4, 1995

[54] PUNCH FOR OPENING PASSAGES BETWEEN TWO COMPARTMENTS

[75] Inventor: Simcha Milo, Haifa, Israel

[73] Assignee: Scanlan International, Inc., St. Paul, Minn.

[21] Appl. No.: 7,345

[22] Filed: Jan. 21, 1993

[30] Foreign Application Priority Data

Jan. 21, 1992 [IL] Israel ................................ 100721

[51] Int. Cl.6 ............................................ A61B 17/32
[52] U.S. Cl. ...................................... 606/184; 604/164
[58] Field of Search ...................... 604/158, 164–168, 604/264; 606/184, 185, 182

[56] References Cited

U.S. PATENT DOCUMENTS

| | | | |
|---|---|---|---|
| 4,018,228 | 4/1977 | Goosen | 606/184 |
| 4,191,191 | 4/1980 | Auburn | 606/185 |
| 4,216,776 | 8/1980 | Downie et al. | 606/184 |
| 5,009,643 | 4/1991 | Reich et al. | 606/185 |
| 5,129,913 | 7/1992 | Ruppert | 606/184 |
| 5,139,503 | 8/1992 | Kantrowitz et al. | 606/184 |
| 5,192,294 | 3/1993 | Blake, III | 606/184 |
| 5,242,427 | 9/1993 | Bilweis | 606/185 |
| 5,258,003 | 11/1993 | Ciaglia et al. | 606/185 |

*Primary Examiner*—Stephen C. Pellegrino
*Assistant Examiner*—William Lewis
*Attorney, Agent, or Firm*—Faegre & Benson

[57] ABSTRACT

A punch for opening passages between two compartments comprises an outer hollow tube and an inner needle tube. The outer hollow tube has a sharp distal edge constituting a circular knife. The needle tube is provided with screw actuating member at a proximal end thereof and a bevelled tip at a distal end thereof. A screw mechanism is located upon a distal end of the needle tube, and the screw mechanism is connected to a cutting disc. The mechanism is screw-actuated by the actuating member. The punch is particularly suitable in cardiac surgery and cardiology as a cardiac catheter and in opening the inter-atrial septum of babies.

20 Claims, 2 Drawing Sheets

PUNCH FOR OPENING PASSAGES BETWEEN TWO COMPARTMENTS

BACKGROUND OF THE INVENTION

The present invention relates to a punch for opening passages between two compartments. Such a tool is in particular suitable in cardiac surgery and cardiology as a cardiac catheter. The invention will be described in connection with said use, however it is not restricted to same.

In cardiac surgery it is very often essential to form passages between various compartments which are blocked. This applies in general for the transfer in each of the arteries and chambers of the heart between same and at their outlet when they are blocked. This is, for example, very important in opening the inter-atrial septum of babies with transposition of the great arteries. Moreover, this is very important in the production of such a passage having a well defined hole in a graft in the heart or at the wall of the artery.

There are known surgical means and methods for the opening of such passages, e.g. the balloon method of Rashkind et al., JAMA 1966; 196; 991-2.

However, all said known devices and methods require rather complicated surgical means and methods. These means and methods are not satisfactory and the mortality rate in some of the operations to be performed with them is quite high, e.g. 47% in the surgery of opening of the inter atrial septum of babies.

It has therefore been desirable to design means which overcome the above drawbacks. Said means should be relatively inexpensive and easy to manufacture and be safe and simple to use.

SUMMARY OF THE INVENTION

The present invention thus consists of a punch comprising:
- an outer hollow tube having a sharp distal edge constituting a circular knife;
- a needle tube provided with actuating means, said needle tube passing through the hollow tube and having a bevelled tip at a distal end of the needle tube; and
- a screw mechanism located upon a distal end of the needle tube, the mechanism connected to a cutting disc, said mechanism screw-actuated by said actuating means.

BRIEF DESCRIPTION OF THE FIGURES

The present invention will now be illustrated with reference to the accompanying drawings, without being restricted by same. Similar parts shown in various drawings will be referenced by the same numeral. In said drawings.

DETAILED DESCRIPTION OF THE INVENTION

Figure 1:
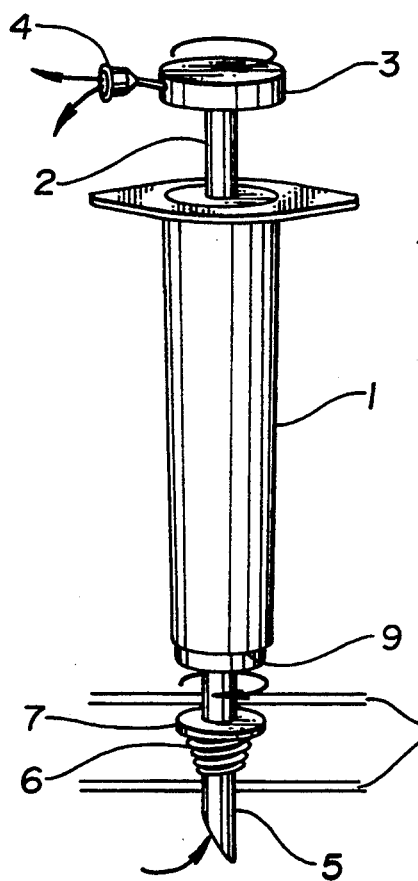
FIG. 1 shows a perspective view of a punch according to the present invention.
Figure 2:
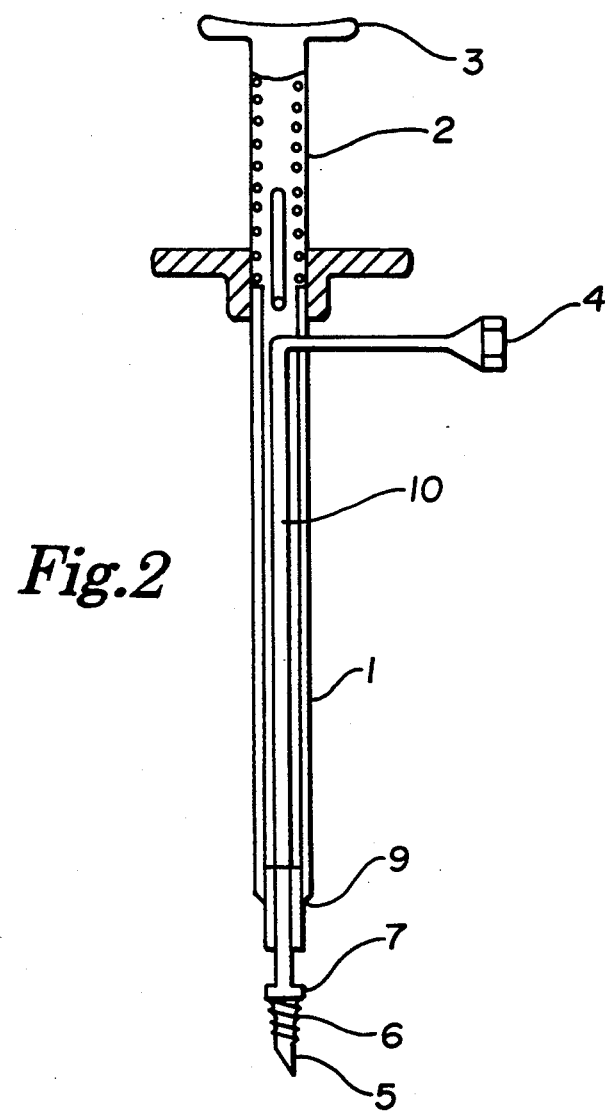
FIG. 2 shows a vertical cross-section of the punch according to the present invention.

The punch illustrated in FIG. 1 comprises hollow tube 1, needle tube 2 passing through hollow tube 1. At the upper end of needle tube 2 is located actuating handle 3, provided with outlet 4. The lower end of needle tube 2 is constituted by tip 5. Upon needle tube 2 is located screwing mechanism 6 to which is connected cutting disc 7. Edge 9 of tube 1 constitutes a circular knife. The inter-atrial septum is reference 8. The punch illustrated in FIG. 1 comprises also channel 10 (seen in FIG. 2 only) for the transfer of blood. Note that, as shown in FIG. 2, outlet 4 may alternatively protrude through the side of tube 1.

Figure 3:
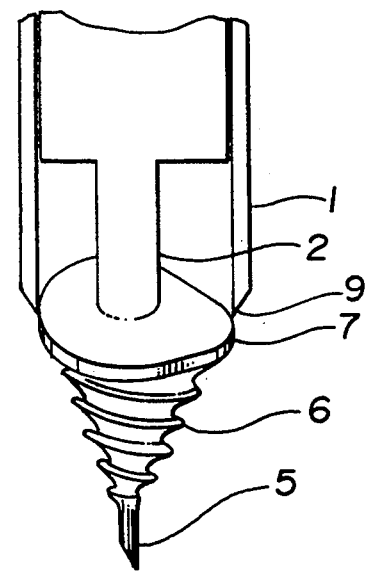
FIG. 3 shows a punch provided with a tear-drop-like cutting disc.

FIGS. 3 through 7 show cutting discs having special forms. In the embodiments shown in FIGS. 1-3, the initial penetration of the tissue is made using the bevelled needle point of tip 5. The site of the penetration (illustrated as the inter-atrial septum 8 in FIG. 1) is then expanded by rotational action of the screwing mechanism 6, in the direction of rotation shown in FIG. 1, until the disc 7 is through the tissue to the side opposite the initial penetration. This position is illustrated in FIG. 1 with the disc 7 and the knife edge 9 of tube 1 on opposite sides of the penetrated surface of the inter-atrial septum 8. The cutting disc 7 may be circular, as shown in FIGS. 1 and 2, or may be of a non-circular tear drop shape, as shown in FIG. 3. The tube 1 and its knife edge 9 will have the same cross-sectional shape as the corresponding cutting disc 7, that is they are both generally circular, as seen in FIGS. 1, 2, 4 and 4a, or are both generally of a tear drop cross-sectional shape, as seen in FIGS. 3 and 3a. With continued advancement of the punch into the tissue, the knife edge 9 of tube 1 cuts through the tissue as the tube 1 is advanced toward cutting disc 7, as illustrated in FIG. 3, thereby forming an aperture in the tissue having the same shape as the cross section of disc 7.

Figure 4:
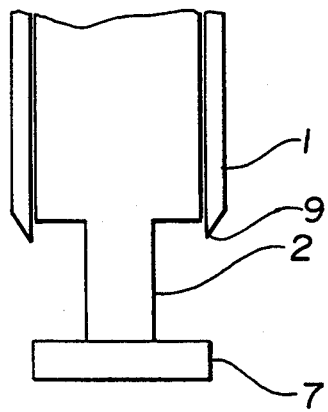
FIG. 4 shows a profile of the punch of FIG. 3.

In an alternative embodiment of the invention, shown in FIGS. 3a, 4 and 4a, the disc 7 can be worked into a pre-formed slit in the tissue or other material to be cut. Cutting occurs as the cutting disc 7 and the circular knife edge 9 of tube 1 move relatively closer together, as illustrated in FIG. 3a, to allow disc 7 to force the material to be cut against the cutting edge 9 of tube 1.

The punch serving as a cardiac catheter is advantageously made of stainless steel. However, it may be made also from suitable materials, e.g. certain rigid plastic materials, etc.

Needle tube 2 may be hollow or, if this is not required, it may be a rod. Needle tube 2 has to be hollow in such cases where channel 10 has to be inserted in same. Channel 10 serves for the flow of blood being taken from the lower left atrium of the heart to the outside in the surgery of the inter-atrial septum of babies, in order to ensure that the needle tip 5 is in the desired compartment and that the passage created will ensure that the blood mixes in the correct ratio. In this case, the punch has to be provided with outlet 4 for the blood from said channel 10.

Figure 5:
FIG. 5 shows the tear-drop shape of the cutting disc of FIGS. 3 and 4.
Figure 6:
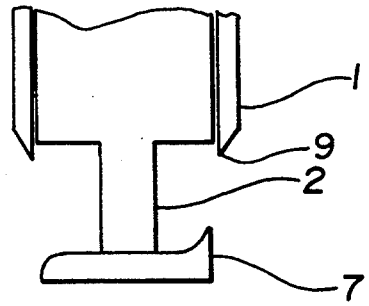
FIG. 6 shows part of a punch provided with a cutting disc with uneven edges.
Figure 8:
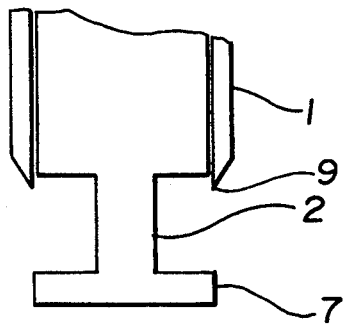
FIG. 8 shows part of a punch provided with a cutting disk wherein the cutting edge is flat.
Figure 7:
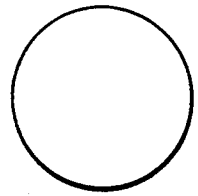
FIG. 7 shows the circular shape of the cutting disk of FIG. 6.
Figure 9:
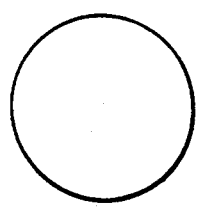
FIG 9 shows the circular shape of the cutting disk of FIG. 8.

Cutting disc 7 may have any suitable cross-section. It may be circular, as shown in FIGS. 6 and 7, tear-drop-like, as shown in FIGS. 3 through 5, etc. The tear-drop-like disc is being used, preferably, for example, for proximal aorta-coronary anastomoses. Cutting disc 7 may be flat, as shown in FIGS. 4, 5, 8 and 9 or have uneven curved cutting edges, as shown in FIG. 6 and 7.

The great advantage of the punch according to the present invention, serving in a cardiac surgery, is that it may be used for many purposes from the outside of the body, and thus serves in a non-surgical manner. The cardiac catheter may be used while the heart is working, or even if it is connected to a heart-lung machine, e.g. in the course of cardiac-pulmonary bypass.

The use of said cardiac catheter ascertains that well defined holes are obtained.

The cardiac catheter according to the present invention operates as follows, e.g. for the opening of the inter atrial septum: the punch is introduced from the patient's groin into the heart and into the right atrium. After it has been properly positioned, needle tube 2 is screwed through the septum into the left atrium. Thereafter, needle tube 2 is retracted, the septum is cut, some tissue is removed and a well defined hole is obtained. Some blood flows through channel 10 within needle tube 2 and the blood received at outlet 4 can be tested.

What is claimed is:

1. A punch comprising
   an outer hollow tube having a sharp distal circumferential cutting edge;
   a needle having a proximal and a distal end, provided on the proximal end of the needle with rotational actuating means, said needle received within the hollow tube and having a bevelled tip at the distal end of the needle; and
   a screw mechanism located upon the distal end of the needle proximal of the bevelled tip, and a cutting disc capable of engaging said cutting edge, said cutting disc located upon the distal end of the needle proximal of the screw mechanism, said screw mechanism and said cutting disc configured for rotation with said needle, said screw mechanism and said cutting disc rotated by rotation of said rotational actuating means.

2. A punch according to claim 1, wherein the needle is hollow.

3. A punch according to claim 2, wherein a channel passes through the needle tube, said channel being provided with an outlet exterior to said punch in fluid flow communication with said channel.

4. A punch according to claim 1, wherein the cutting disc is circular.

5. A punch according to claim 1, wherein the cutting disc is tear-drop-like.

6. A punch according to claim 4, wherein the cutting disc is flat.

7. A punch according to claim 4, wherein the cutting disc is uneven.

8. A punch according to claim 5, wherein the cutting disc is flat.

9. A punch according to claim 5, wherein the cutting disc is uneven.

10. A method for punching an aperture in a tissue using a punch according to claim 1 comprising:
    forming an initial penetration of the tissue with the needle bevelled tip;
    rotationally advancing the screw mechanism to expand the initial penetration until the cutting disc passes through the tissue to a side opposite the initial penetration; and
    continuing to advance the punch until the sharp distal cutting edge cuts through the tissue, thereby forming an aperture in the tissue having a cross-sectional shape of the cutting disc.

11. A punch comprising:
    a hollow tube having a proximal and a distal end, said distal end constituting a knife cutting edge;
    a needle having a proximal and a distal end slidably received within the hollow tube, the needle distal end configured with a terminal bevelled tip, with a screw thread proximal of the bevelled tip, and with a cutting disc proximal of the screw thread, said cutting disc capable of engaging the knife cutting edge, the needle proximal end provided with a handle for screw rotating the bevelled tip, the screw thread and the cutting disc therewith.

12. A punch according to claim 11, wherein the needle has a hollow interior.

13. A punch according to claim 12, wherein the needle is provided with an outlet in fluid flow communication with the hollow interior.

14. A punch according to claim 11, wherein the cutting disc is circular.

15. A punch according to claim 14, wherein the cutting disc is flat.

16. A punch according to claim 14, wherein the cutting disc is uneven, such that only a portion of a cutting edge thereof comes into contact with material to be cut, and such that cutting is achieved between the cutting disc and the knife cutting edge at the distal end of the tube.

17. A punch according to claim 11, wherein the cutting disc is tear-drop-like.

18. A punch according to claim 17, wherein the cutting disc is flat.

19. A punch according to claim 17, wherein the cutting disc is uneven.

20. A method for punching an aperture in a material using a punch according to claim 10 comprising:
    forming an initial penetration of the material with the needle bevelled tip;
    rotationally advancing the screw thread to expand the initial penetration until the cutting disc passes through the material to a side opposite the initial penetration; and
    continuing to advance the punch until the knife cutting edge cuts through the material, thereby forming an aperture in the material having a cross-sectional shape of the cutting disc.

* * * * *